US008723676B2

(12) United States Patent
Su et al.

(10) Patent No.: US 8,723,676 B2
(45) Date of Patent: May 13, 2014

(54) REHABILITATION-ASSISTING APPARATUS

(75) Inventors: Mu-Chun Su, Taoyuan County (TW); Jhih-Jie Jhang, Taoyuan County (TW); Tun-Ya Yu, Taoyuan County (TW); Yi-Zeng Hsieh, Taoyuan County (TW); Shih-Chieh Lin, Taoyuan County (TW)

(73) Assignee: National Central University, Taoyuan County (TW)

( * ) Notice: Subject to any disclaimer, the term of this patent is extended or adjusted under 35 U.S.C. 154(b) by 266 days.

(21) Appl. No.: 13/273,229

(22) Filed: Oct. 14, 2011

(65) Prior Publication Data

US 2013/0015969 A1 Jan. 17, 2013

(30) Foreign Application Priority Data

Jul. 12, 2011 (TW) .............................. 100124662 A

(51) Int. Cl.
*G08B 23/00* (2006.01)
(52) U.S. Cl.
USPC ................. 340/573.7; 340/573.1; 340/539.11
(58) Field of Classification Search
USPC ....................................................... 340/573.7
See application file for complete search history.

(56) References Cited

U.S. PATENT DOCUMENTS

| 6,145,389 | A  | * | 11/2000 | Ebeling et al. ................ 73/865.4 |
| 6,621,418 | B1 | * | 9/2003  | Cayrol ......................... 340/573.1 |
| 7,857,771 | B2 | * | 12/2010 | Alwan et al. ................... 600/595 |
| 2004/0113815 | A1 | * | 6/2004 | Newcomer ................. 340/932.2 |
| 2005/0184878 | A1 | * | 8/2005 | Grold et al. ................. 340/573.7 |
| 2007/0112287 | A1 | * | 5/2007 | Fancourt et al. .............. 600/595 |
| 2012/0254934 | A1 | * | 10/2012 | McBrearty et al. ........... 725/118 |

FOREIGN PATENT DOCUMENTS

| TW | M369462   | 11/2009 |
| TW | 201106677 | 2/2011  |

* cited by examiner

*Primary Examiner* — Kerri McNally
(74) *Attorney, Agent, or Firm* — CKC & Partners Co., Ltd.

(57) ABSTRACT

A rehabilitation-assisting apparatus is provided in this disclosure. The rehabilitation-assisting apparatus includes at least one step-information sensing unit, an alert-signal generating unit and a processing unit. The step-information sensing unit can be worn on a user's lower limb. The step-information sensing unit senses and generates step information of the user. The processing unit builds connections with the step-information sensing unit and the alert-signal generating unit. The processing unit determines if the user is walking appropriately according to the step information of the user. The processing unit drives the alert-signal generating unit to generate an alert signal when the user is not walking appropriately.

11 Claims, 3 Drawing Sheets

REHABILITATION-ASSISTING APPARATUS

RELATED APPLICATIONS

This application claims priority to Taiwan Application Serial Number 100124662 filed Jul. 12, 2011, which is herein incorporated by reference.

BACKGROUND

1. Technical Field

The present invention relates to a rehabilitation-assisting apparatus.

2. Description of Related Art

Many middle-aged persons and senior citizens suffer from Parkinson's is disease, cerebrovascular accidents (CVAs), and Alzheimer's disease (AD). In Taiwan, most cases occur after the age of 60, and the possibility of encountering such health problems rises with increased age. With the average age of populations around the world increasing, more and more people are suffering from Parkinson's disease.

Parkinson's disease is a degenerative disorder of the central nervous system. Parkinson's disease damages abilities related to movement, language and some other functions. Parkinson's patients may walk with a Parkinsonian gait and may experience a freezing of gait. Patients with a Parkinsonian gait may tilt their upper bodies and take short or shuffling steps as they walk. Freezing of gait refers to the situation in which patients may freeze suddenly during walking. Such symptoms may affect a patient's walking ability, such that the patient avoids going outdoors to interact with other people or to enjoy nature, ultimately damaging the patient's physical and mental health.

As a result, there is a need to assist Parkinson's patients for rehabilitation.

SUMMARY

According to one embodiment of this invention, a rehabilitation-assisting apparatus is provided. A sensing unit of the rehabilitation-assisting apparatus can be worn on a user's lower limb to sense and generate step information of the user, which may be used to determine if the user is walking appropriately.

The rehabilitation-assisting apparatus includes at least one step-information sensing unit, an alert-signal generating unit and a processing unit. The processing unit builds connections with the step-information sensing unit and the alert-signal generating unit. The step-information sensing unit can be worn on a user's lower limb. The step-information sensing unit senses and generates step information of the user. The processing unit includes a step-information receiving module, a determining module and an alert module. The step-information receiving module receives the step information of the user from the step-information sensing unit. The determining module determines if the user is walking appropriately according to the step information of the user. The alert module drives the alert-signal generating unit to generate an alert signal when the user is not walking appropriately.

The present invention can achieve many advantages. The rehabilitation-assisting apparatus can alert users when they do not walk appropriately, which can provide assistance for rehabilitation. In addition, the rehabilitation-assisting apparatus can alert users when they cross their steps or when the height of their steps is too low, which can assist Parkinson's patients for rehabilitation. Furthermore, a projected virtual cueing line can be a target for patients to step across. In some embodiments, a virtual cueing line can be displayed using projection techniques, which would not block a user's sight. Additionally, users and their doctors can review the step information stored in the storage unit for adjusting rehabilitation schedules.

These and other features, aspects, and advantages of the present invention will become better understood with reference to the following description and appended claims. It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiments, with reference made to the accompanying drawings as follows.

DETAILED DESCRIPTION

Figure 1:
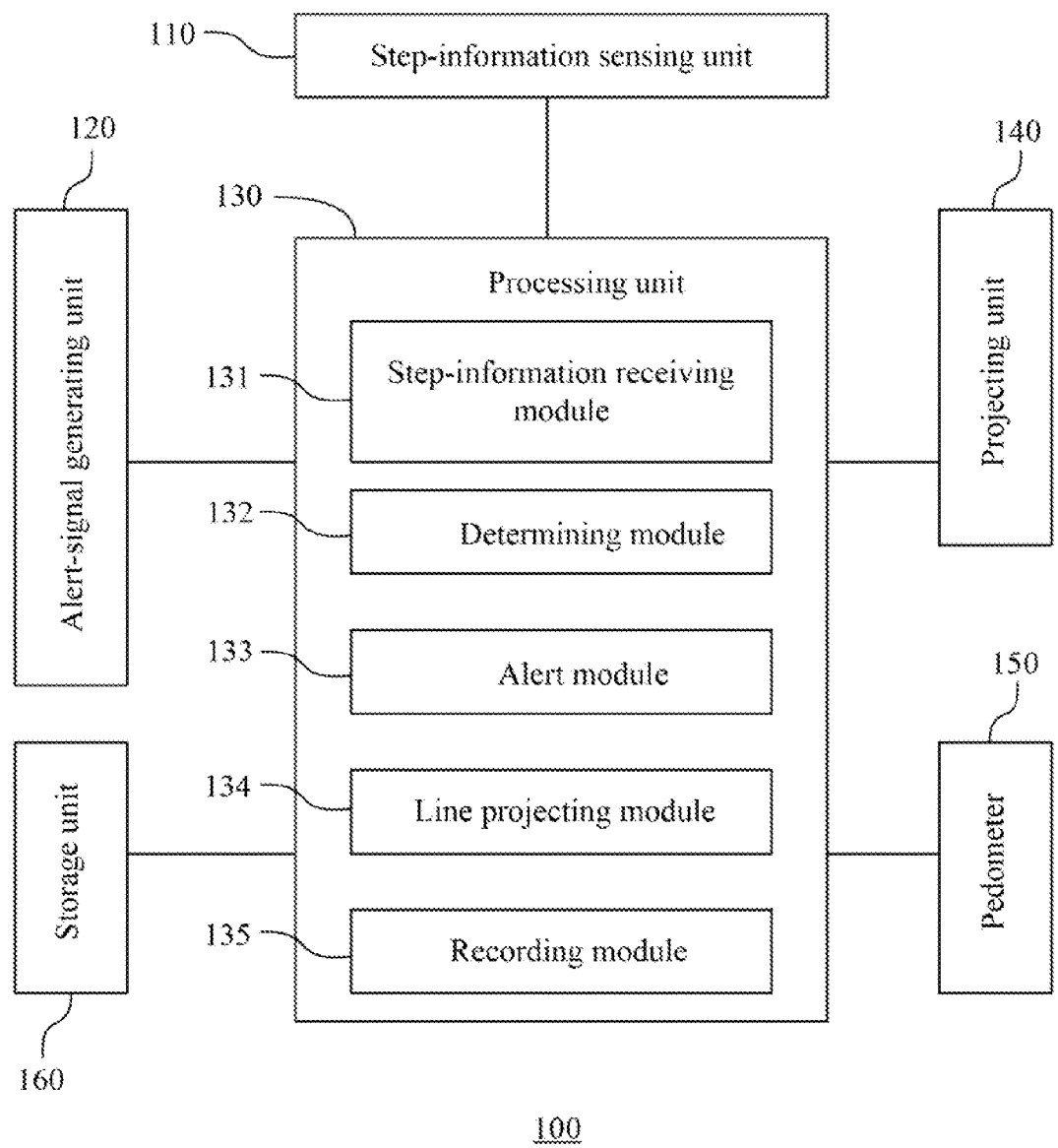
FIG. 1 is a block diagram of a rehabilitation-assisting apparatus according to an embodiment of this invention.

Reference will now be made in detail to the present embodiments of the invention, examples of which are illustrated in the accompanying drawings. Wherever possible, the same reference numbers are used in the drawings and the description to refer to the same or like parts.

Referring to FIG. 1, a block diagram will be described that illustrates a rehabilitation-assisting apparatus according to an embodiment of this invention. A sensing unit of the rehabilitation-assisting apparatus can be worn on a user's lower limb to sense and generate the user's steps information, and the step information may be used to determine if the user is walking appropriately.

The rehabilitation-assisting apparatus 100 includes at least one step-information sensing unit 110, an alert-signal generating unit 120 and a processing unit 130. The processing unit 130 builds connections with the step-information sensing unit 110 and the alert-signal generating unit 120 through a wired or wireless data transmission interface.

Figure 2:
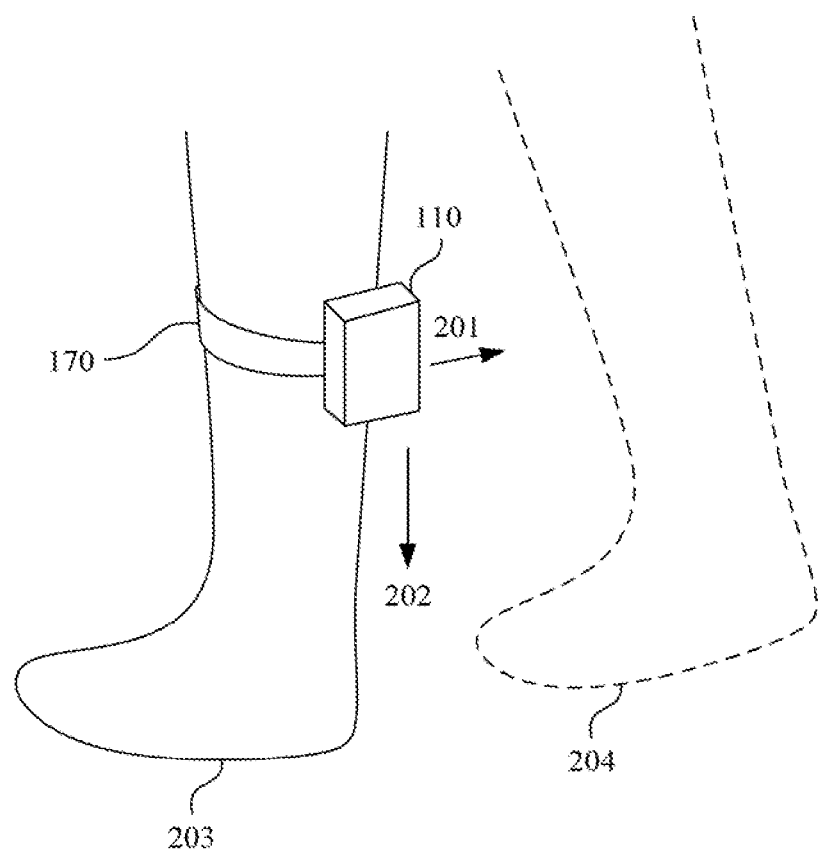
FIG. 2 illustrates an embodiment in which a step-information sensing unit of the rehabilitation-assisting apparatus in FIG. 1 is worn on a user's lower limb.

The step-information sensing unit 110 can be worn on a user's lower limb (for example, the user's foot, ankle, or lower leg). The step-information sensing unit 110 senses and generates step information of the user. The step information of the user may include step height of the user, information for determining if the user crosses his/her steps or any other information for determining if the user's steps are normal. FIG. 2 illustrates an embodiment in which the step-information sensing unit 110 is worn on a user's lower limb 203. The step-information sensing unit 110 can be worn on a user's lower limb 203 utilizing a wearing piece 170. The wearing piece 170 may be a belt or any other object, which can fasten the step-information sensing unit 110 on a user's lower limb 203. In another embodiment of this invention, the rehabilitation-assisting apparatus 100 may include two step-information sensing units, which are worn respectively on both lower limbs of a user.

The processing unit 130 includes a step-information receiving module 131, a determining module 132 and an alert module 133. The step-information receiving module 131 receives the step information of the user from the step-information sensing unit 110. The determining module 132 determines if the user is walking appropriately according to the step information of the user. When the user is not walking appropriately, the alert module 133 drives the alert-signal generating unit 120 to generate an alert signal. The alert-signal generating unit 120 may be a speaker, a light or any other type of device capable of generating a signal to alert the user. The alert signal generated may be an alert sound, an alert light signal or any other type of signal capable of attracting the attention of the user. Therefore, when the user is not walking appropriately, the rehabilitation-assisting apparatus 100 can notify the user with an alert signal to assist the user for rehabilitation.

The step-information sensing unit 110 may be a distance sensing unit. When the distance sensing unit (step-information sensing unit) 110 senses that a distance between a neighboring object and the distance sensing unit 110 is less than a distance threshold (indicating that a distance between the neighboring object and the area of the lower limb 203 where the distance sensing unit 110 is worn is less than the distance threshold), a close-proximity signal is generated and included in the step information of the user. When step information with the close-proximity signal is received, the determining module 132 determines that the user is not walking appropriately. In one embodiment of this invention, when the distance sensing unit (step-information sensing unit) 110 is worn on a user's lower limb 203 utilizing the wearing piece 170, the distance sensing unit 110 senses if there is a neighboring object in the rearward direction 201 of the user's lower limb 203 within the distance threshold. Therefore, when the user crosses one of his/her lower limb 203 in front of the other lower limb 204, which would result in a smaller sensed distance, that is, a sensed distance smaller than the distance threshold, the alert signal can notify is the user that his or her steps are crossed.

In another embodiment of this invention, when the distance sensing unit (step-information sensing unit) 110 is worn on a user's lower limb utilizing the wearing piece 170, the distance sensing unit 110 senses if there is a neighboring object in the downward direction 202 of the user's lower limb 203 within the distance threshold. Therefore, when the user's step is too low, which would result in a smaller sensed distance without break, that is, a sensed distance smaller than the distance threshold keeping sensed without break, the alert signal can notify the user to raise his or her steps.

In addition, the step-information sensing unit 110 may be an interruption sensing unit, such as an ultrasonic sensor, an Infrared (Ir) interrupter sensor, an optical interruption sensor or any other type of sensor capable of interruption sensing. When the interruption sensing unit (step-information sensing unit) 110 is interrupted, the interruption sensing unit 110 generates an interruption signal to be included in the step information of the user. Hence, when step information with the interruption signal is received, the determining module 132 determines that the user is not walking appropriately. In one embodiment of this invention, when the interruption sensing unit (step-information sensing unit) 110 is worn on a user's lower limb utilizing the wearing piece 170, the interruption sensing unit 110 senses if there is a neighboring object causing an is interruption from the rearward direction 201 of the user's lower limb 203. Therefore, when the user crosses one of his/her lower limbs 203 in front of the other lower limb 204, which would result in interruption by the lower limb 204, the alert signal, which is generated due to the interruption, can notify the user that his or her steps are crossed.

In another embodiment of this invention, when the interruption sensing unit (step-information sensing unit) 110 is worn on a user's lower limb utilizing the wearing piece 170, the interruption sensing unit 110 senses if there is a neighboring object causing an interruption from the downward direction 202 of the user's lower limb 203. Therefore, when the user's step is too low, which would result in interruption by the ground without break, the alert signal, which is generated due to the interruption without break, can notify the user to raise his or her steps.

Furthermore, the rehabilitation-assisting apparatus 100 may further include a projecting unit 140. The projecting unit 140 may build a connection with the processing unit 130 through a wired or wireless data transmission interface. The processing unit 130 may further include a line projecting module 134.

Figure 3:
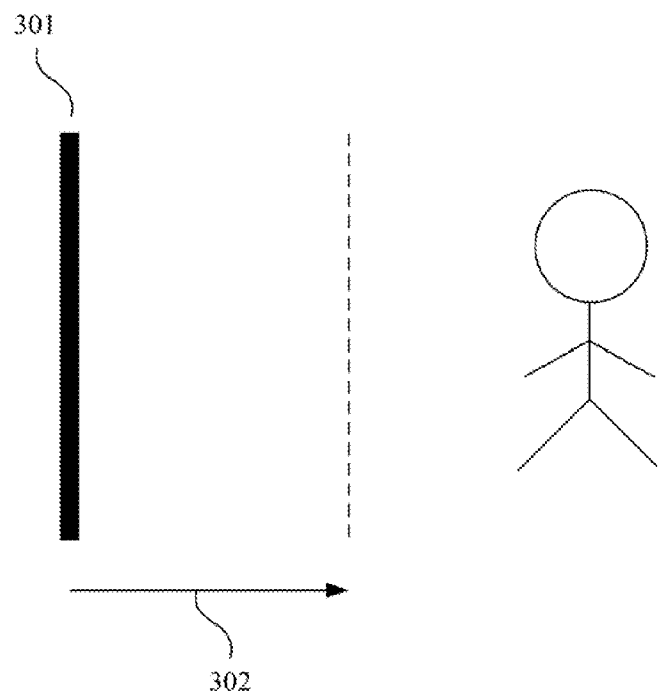
FIG. 3 illustrates a schematic diagram of a virtual cueing line projected by a projecting unit of the rehabilitation-assisting apparatus in FIG. 1 according to an embodiment of this invention.

FIG. 3 illustrates a schematic diagram of a virtual cueing line 301 projected by the projecting unit 140 according to an embodiment of the present invention. In this embodiment, the line projecting module 134 may drive the projecting unit 140 to project at least one virtual cueing line 301, which moves in a direction 302 toward the user. Therefore, the user can use the virtual cueing line 301 as a target to stride across while proceeding in a straight direction, which can assist the user to walk. In some embodiments, a new cueing line 301 that is moved in the direction 302 toward the user can be repeatedly projected with a predetermined interval between each new cueing line 301. As a result, the virtual cueing line 301 may be perceived by users as stretching limitlessly along their routes. Furthermore, users can set the moving speed for the virtual cueing line 301 according to their own rehabilitation schedule, which may assist users to eventually walk as normal persons at the end of rehabilitation. In embodiments where a new virtual cueing line 301 is repeatedly projected, the intervals between the virtual cueing lines 301 can be set according to the rehabilitation schedule of the user. In addition, since the virtual cueing line 301 is displayed by projection, a user's sight is not blocked.

Figure 4:
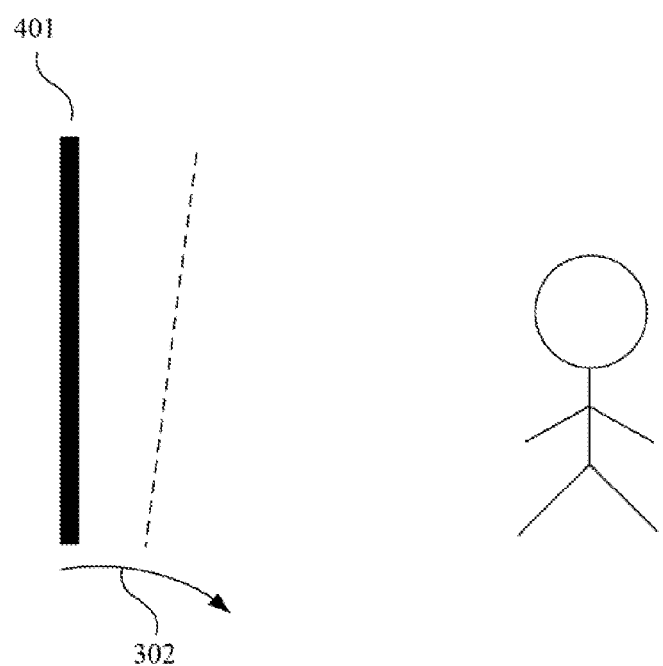
FIG. 4 illustrates a schematic diagram of a virtual cueing line projected by the projecting unit of the rehabilitation-assisting apparatus in FIG. 1 according to another embodiment of this invention.

FIG. 4 illustrates a schematic diagram of a virtual cueing line 401 projected by the projecting unit 140 according to another embodiment of this invention. In this embodiment, the line projecting module 134 may drive the projecting unit 140 to project at least one virtual cueing line 401 that moves toward the user with a predetermined curvature 402. Therefore, users can use the virtual cueing line 401 as a target to stride across while walking in a curved direction, which can assist the user to walk when turning.

The rehabilitation-assisting apparatus 100 may generates sounds with a regular pattern like a metronome. Hence, users can walk steadier with the assistance of the virtual cueing line 301, 401 moving at a fixed speed and with sounds that are regularly patterned.

The rehabilitation-assisting apparatus 100 may further include a pedometer 150. The pedometer 150 may build a connection with the processing unit 130 through a wired or wireless data transmission interface. The pedometer 150 is utilized for generating step-counting information of a user. The line projecting module 134 calculates a line moving speed according to the step-counting information and drives the projecting unit 140 to project at least one virtual cueing line 301, 401 moving toward the user at the line moving speed. Therefore, the virtual cueing line 301, 401 can move toward the user at the speed corresponding to the speed at which the user walks.

The rehabilitation-assisting apparatus 100 may further include a storage unit 160 electrically connected to the processing unit 130, and the processing unit 130 further includes a recording module 135. When it is determined that the user is not walking appropriately, the recording module 135 records step information in the storage unit 160. Therefore, patients and their doctors can review the step information stored in the storage unit 160 for adjusting rehabilitation schedules.

The present invention can achieve many advantages. The rehabilitation-assisting apparatus can alert users when they do not walk appropriately, which can provide assistance for rehabilitation. In addition, the rehabilitation-assisting apparatus can alert users when they cross their steps or when the height of their steps is too low, which can assist Parkinson's patients for rehabilitation. Furthermore, a projected virtual cueing line can be a target for patients to step across. In some embodiments, a virtual cueing line can be displayed using projection techniques, which would not block a user's sight. Additionally, users and their doctors can review the step information stored in the storage unit for adjusting rehabilitation schedules.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present is invention cover modifications and variations of this invention provided they fall within the scope of the following claims.

What is claimed is:

1. A rehabilitation-assisting apparatus comprising:
   at least one step-information sensing unit to be worn on a user's lower limb, wherein the step-information sensing unit senses and generates step information of the user, wherein the step-information sensing unit detects distance, wherein when the step-information sensing unit senses that a distance between a neighboring object and the user's lower limb is less than a distance threshold, a close-proximity signal is generated and included in the step information of the user;
   an alert-signal generating unit; and
   a processing unit building connections with the step-information sensing unit and the alert-signal generating unit, the processing unit receives the step information of the user from the step-information sensing unit, wherein when the processing unit receives the step information with the close-proximity signal, the processing unit determines that the user is not walking appropriately, and the processing unit drives the alert-signal generating unit to generate an alert signal.

2. The rehabilitation-assisting apparatus of claim 1 further comprising:
   a wearing piece, wherein the step-information sensing unit senses if there is a neighboring object in the rearward direction of the user's lower limb within the distance threshold when the step-information sensing unit is worn on the user's lower limb utilizing the wearing piece.

3. The rehabilitation-assisting apparatus of claim 1 further comprising:
   a wearing piece, wherein the step-information sensing unit senses if there is a neighboring object in the downward direction of the user's lower limb within the distance threshold when the step-information sensing unit is worn on the user's lower limb utilizing the wearing piece.

4. The rehabilitation-assisting apparatus of claim 1, wherein:
   the step-information sensing unit further performs interruption sensing,
   when the step-information sensing unit is interrupted, the step-information sensing unit generates an interruption signal to be included in the step information of the user,
   when step information with the interruption signal is received, the determining module determines that the user is not walking appropriately.

5. The rehabilitation-assisting apparatus of claim 4, wherein the step-information sensing unit is an ultrasonic sensor, an Infrared (Ir) interrupter sensor or an optical interruption sensor.

6. The rehabilitation-assisting apparatus of claim 4 further comprising:
   a wearing piece, wherein the step-information sensing unit senses if there is a neighboring object causing an interruption from the rearward direction of the user's lower limb when the step-information sensing unit is worn on the user's lower limb utilizing the wearing piece.

7. The rehabilitation-assisting apparatus of claim 4 further comprising:
   a wearing piece, wherein the step-information sensing unit senses if there is a neighboring object causing an interruption from the downward direction of the user's lower limb when the interruption sensing unit is worn on the user's lower limb utilizing the wearing piece.

8. The rehabilitation-assisting apparatus of claim 1 further comprising:
   a projecting unit building a connection with the processing unit,
   wherein the processing unit drives the projecting unit to project at least one virtual cueing line, which moves toward the user.

9. The rehabilitation-assisting apparatus of claim 1 further comprising:
   a projecting unit building a connection with the processing unit,
   wherein the processing unit drives the projecting unit to project at least one virtual cueing line moving toward the user with a predetermined curvature.

10. The rehabilitation-assisting apparatus of claim 1 further comprising:
    a projecting unit building a connection with the processing unit; and
    a pedometer building a connection with the processing unit, wherein the pedometer is utilized for generating step-counting information,
    wherein the processing unit calculates a line moving speed according to the step-counting information and to drive the projecting unit to project at least one virtual cueing line moving toward the user at the line moving speed.

11. The rehabilitation-assisting apparatus of claim 1 further comprising:
    a storage unit electrically connected to the processing unit,
    wherein the processing unit records step information to the storage unit when the user is not walking appropriately.

* * * * *